(12) United States Patent
McNulty

(10) Patent No.: US 9,494,632 B1
(45) Date of Patent: Nov. 15, 2016

(54) HIGH-VOLTAGE DETECTOR MONITORING SYSTEM

(71) Applicant: HD Electric Company, Waukegan, IL (US)

(72) Inventor: William J. McNulty, Washington, DC (US)

(73) Assignee: HD Electric Company, Waukegan, IL (US)

( * ) Notice: Subject to any disclaimer, the term of this patent is extended or adjusted under 35 U.S.C. 154(b) by 32 days.

(21) Appl. No.: 14/503,350

(22) Filed: Sep. 30, 2014

Related U.S. Application Data

(60) Provisional application No. 61/885,496, filed on Oct. 1, 2013.

(51) Int. Cl.
  *G08B 21/00* (2006.01)
  *G01R 29/08* (2006.01)
  *A61B 5/00* (2006.01)

(52) U.S. Cl.
  CPC .......... *G01R 29/0857* (2013.01); *A61B 5/0006* (2013.01)

(58) Field of Classification Search
  CPC ............ A61B 19/44; A61B 2019/442; A61B 2019/448; A61B 5/117; A61B 5/6831; A61B 10/0012; A61B 2010/0019; A61B 2560/0209; A61B 2560/0214; A61B 2560/0412; A61B 2560/045; A61B 5/0006; A61B 5/0008
  USPC ....... 340/660, 552, 649, 601, 662, 628, 449, 340/661
  See application file for complete search history.

(56) References Cited

U.S. PATENT DOCUMENTS

| | | |
|---|---|---|
| 3,309,690 A | 3/1967 | Moffitt |
| 3,369,175 A | 2/1968 | Morris |
| 3,774,110 A | 11/1973 | Roveti |
| 3,786,468 A | 1/1974 | Moffitt |
| 3,878,459 A | 4/1975 | Hanna |
| 4,006,409 A | 2/1977 | Adams |
| 4,349,783 A | 9/1982 | Robson et al. |
| 4,350,951 A | 9/1982 | Jasper |
| 4,605,905 A | 8/1986 | Aslan |
| 4,649,375 A | 3/1987 | Duppong et al. |
| 5,093,651 A | 3/1992 | Thomas |
| 5,103,165 A | 4/1992 | Sirattz |

(Continued)

OTHER PUBLICATIONS

International Search Report and Written Opinion for PCT/US14/58694 mailed Dec. 23, 2014.

*Primary Examiner* — Daniel Previl
(74) *Attorney, Agent, or Firm* — McDonnell Boehnen Hulbert & Berghoff LLP

(57) ABSTRACT

A mechanism for providing monitoring of electric field detectors. In accordance with instructions on a machine-readable medium, a computing system receives from a device data corresponding to a user identifier. Further, the computing device identifies from a plurality of electric field detectors one or more electric field detectors associated with the user identifier and identifies status data for each of the identified one or more electric field detectors. The status data for each electric field detector in the plurality of electric field detectors comprises data indicative of at least (i) a location of the electric field detector and (ii) an alarm state of the electric field detector. Additionally, the computing system causes a display component of the device to display a graphical user interface that presents indicia of the status data for each of the identified one or more electric field detectors.

20 Claims, 11 Drawing Sheets

(56) References Cited

U.S. PATENT DOCUMENTS

| | | | |
|---|---|---|---|
| 5,168,265 A | 12/1992 | Aslan | |
| 5,252,912 A * | 10/1993 | Merritt | G01R 29/085 324/72 |
| 5,256,960 A | 10/1993 | Novini | |
| 5,363,045 A | 11/1994 | Martin et al. | |
| 5,373,284 A | 12/1994 | Aslan | |
| 5,373,285 A | 12/1994 | Aslan | |
| 5,414,344 A | 5/1995 | Chinn | |
| 5,600,307 A | 2/1997 | Aslan | |
| 5,666,949 A | 9/1997 | Debe et al. | |
| 5,708,970 A | 1/1998 | Newman et al. | |
| 6,329,924 B1 * | 12/2001 | McNulty | G01R 29/0857 340/552 |
| 2004/0080320 A1 | 4/2004 | Golub | |
| 2005/0264427 A1 * | 12/2005 | Zeng | H02H 5/12 340/635 |
| 2007/0052537 A1 | 3/2007 | Stults et al. | |
| 2009/0174370 A1 * | 7/2009 | Gilling | G01R 31/3665 320/160 |
| 2010/0067488 A1 * | 3/2010 | Sashihara | H04W 36/36 370/331 |
| 2010/0284545 A1 | 11/2010 | Dietz | |
| 2012/0095926 A1 * | 4/2012 | Nishimura | G06Q 10/103 705/301 |
| 2013/0010110 A1 * | 1/2013 | Kalokitis | G01C 7/04 348/143 |
| 2013/0218681 A1 | 8/2013 | Haney | |

* cited by examiner

| | | |
|---|---|---|
| ● | B. Smith 9/23/2014 7:35 pm<br>SE Corner 2nd Ave. & Park St. | 98A |
| ◐ | T. Johnson 9/23/2014 7:36 pm<br>110 2nd Ave. | 98B |
| ○ | J. Doe 9/23/2014 7:35 pm<br>NW Corner 2nd Ave. & Main St. | 98C |
| ◐ | B. Jackson 9/23/2014 7:34 pm<br>430 Halstead St. | 98D |
| ○ | A. Davis 9/23/2014 7:36 pm<br>713 Jackson Blvd. | 98E |

MAP  LIST

FIG. 5E

HIGH-VOLTAGE DETECTOR MONITORING SYSTEM

CROSS-REFERENCE TO RELATED APPLICATION

Priority is claimed to U.S. Provisional Patent Application No. 61/885,496 filed on Oct. 1, 2013, the contents of which are hereby incorporated by reference.

BACKGROUND

Transmission lines route high-voltage (e.g., 2,000 volts and higher) electrical power from power plants to main or regional stations and to local substations. Distribution lines route high-voltage electrical power from substations to end users. Many such lines and supporting electrical equipment are above ground and thus may be exposed to the elements, requiring frequent inspection, repair, and/or maintenance.

Contact with any high-voltage power lines, whether above ground or below, can be lethal for workers performing such tasks. Thus, workers typically wear monitors or detectors configured to sense the proximity to high-voltage power sources and to responsively alarm or otherwise warn such workers before they reach a dangerous proximity to the high-voltage power source.

One such type of detector senses the electrical field surrounding a live high-voltage conductor, the strength and extent of such fields being proportional to the voltage level. Such detectors typically provide an audible alarm and/or a visible indication of the detected field to warn the user.

SUMMARY

A first non-transitory computer readable medium is disclosed. Stored on the non-transitory computer readable medium are instructions executable by a computing system to carry out functions, including receiving from a device data corresponding to a user identifier, identifying from a plurality of electric field detectors one or more electric field detectors associated with the user identifier, identifying status data for each of the identified one or more electric field detectors, and causing a display component of the device to display a graphical user interface that presents indicia of the status data for each of the identified one or more electric field detectors. In practice, the status data for each electric field detector in the plurality of electric field detectors comprises data indicative of at least (i) a location of the electric field detector and (ii) an alarm state of the electric field detector.

A second non-transitory computer readable medium is also disclosed. Stored on the non-transitory computer readable medium are instructions executable by a computing system to carry out functions, including receiving an indication of a magnitude of a detected electric field; determining that the magnitude of the detected electric field is greater than or equal to at least a threshold magnitude, and responsive to determining the that the magnitude of the detected electric field is greater than or equal to at least the threshold magnitude, (i) generating an alarm signal that includes data indicative of the magnitude of the detected electric field, and (ii) transmitting the alert signal to a remote device.

An electric field detector is disclosed as well. The electric field detector comprises an electric field detection component configured (i) to detect an electric field having a magnitude that is greater than or equal to at least a first threshold magnitude and (ii) to provide at least one output indicative of a magnitude of a detected electric field when the magnitude of the detected electric field is greater than or equal to the first threshold voltage. The electric field detector also includes a communication interface configured to communicate with a remote device. The electric field detector further includes a controller configured to transmit via the communication interface an alarm signal in response to the electric field detection component providing the at least one output. The alarm signal includes data indicative of the magnitude of the detected electric field.

A first method is also disclosed. The first method includes receiving from a device data corresponding to a user identifier. The first method also includes identifying from a plurality of electric field detectors one or more electric field detectors associated with the user identifier. Additionally, the first method includes identifying status data for each of the identified one or more electric field detectors, with the status data for each electric field detector in the plurality of electric field detectors comprising data indicative of at least (i) a location of the electric field detector and (ii) an alarm state of the electric field detector. Further, the first method includes causing a display component of the device to display a graphical user interface that presents indicia of the status data for each of the identified one or more electric field detectors.

Further, a second method is disclosed. The second method includes detecting, by an electric field detector, an electric field having a magnitude that is greater than at least a threshold magnitude. Responsive to detecting the electric field, the second method further includes (i) generating by the electric field detector an alarm signal that includes data indicative of the magnitude of the detected electric field, and (ii) transmitting the alert signal from the electric field detector to a remote device.

Additionally, an apparatus is disclosed. The apparatus comprises at least one processor, the at least one processor being configured to cause the apparatus to: receive from a device data corresponding to a user identifier; identify from a plurality of electric field detectors one or more electric field detectors associated with the user identifier; identify status data for each of the identified one or more electric field detectors, wherein the status data for each electric field detector in the plurality of electric field detectors comprises data indicative of at least (i) a location of the electric field detector and (ii) an alarm state of the electric field detector; and cause a display component of the device to display a graphical user interface that presents indicia of the status data for each of the identified one or more electric field detectors.

These as well as other aspects and advantages will become apparent to those of ordinary skill in the art by reading the following detailed description, with reference where appropriate to the accompanying drawings. Further, this summary is merely an example and is not intended to limit the scope of the invention as claimed.

BRIEF DESCRIPTION OF THE FIGURES

FIGS. 5A, 5B, 5C, 5D, and 5E each show an example display of a graphical user interfaces that may be presented on a display component of a device.

DETAILED DESCRIPTION

Figure 1:
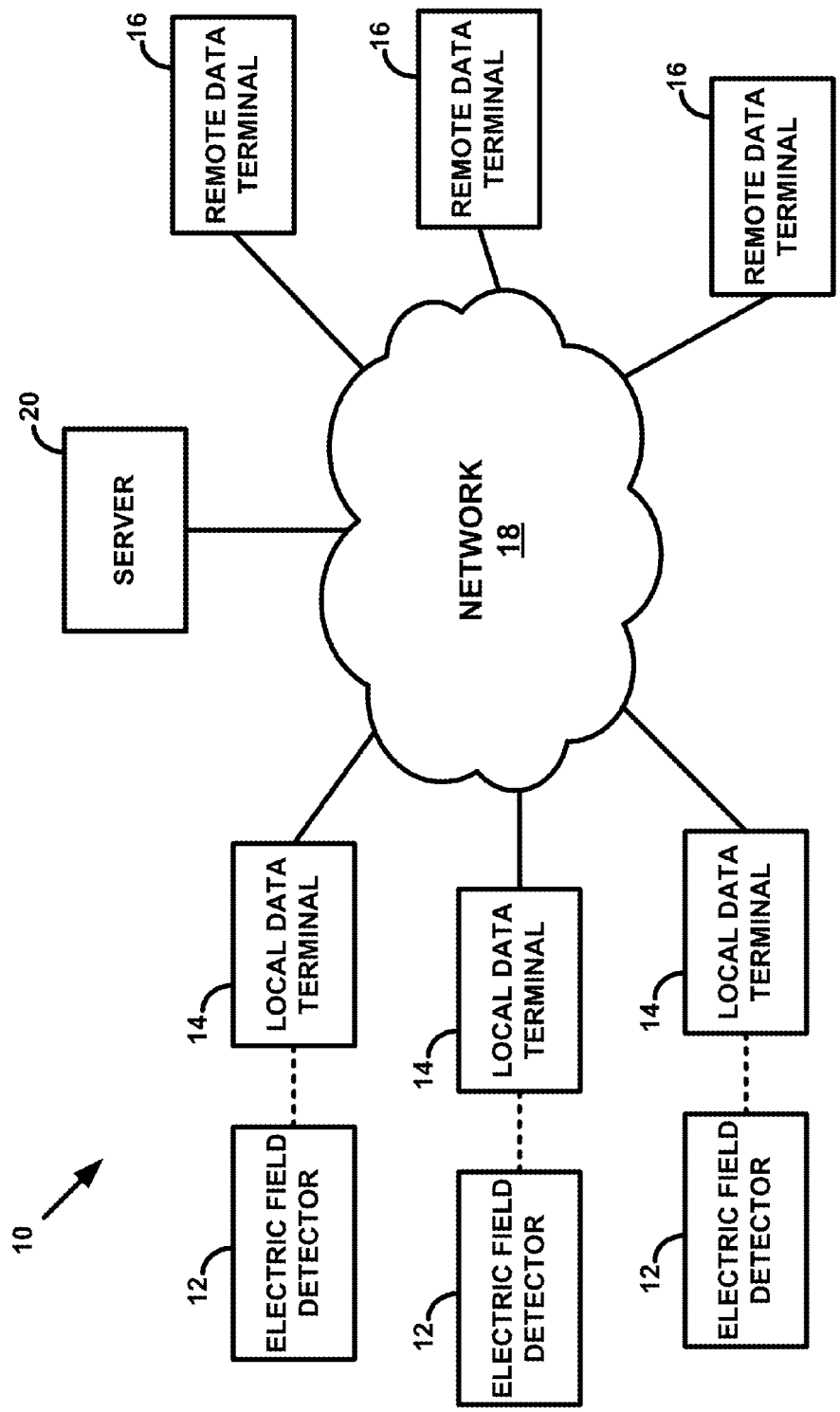
FIG. 1 is an overview of an example system in which features of the present disclosure can be implemented.

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

When working in the vicinity of a high-voltage power source, or when working in an area in which a high-voltage power source may be present, a worker may wear an electric field detector. The electric field detector may be configured to provide one or more different alarms based on a sensed proximity to an electric field of a high-voltage power source. For instance, the electric field detector may provide a different alarm or set of alarms when a detected magnitude of an electric field exceeds any one of a number of threshold magnitudes.

Disclosed herein is a technological mechanism (e.g., a method, apparatus, or system) for monitoring a plurality of electric field detectors. In accordance with the present disclosure, a central computer, such as a server or a cloud-based computing system, may run a detector monitoring program, thereby providing a graphical user interface for monitoring a status of one or more electric field detectors.

While running the detector management program, the central computer may receive and store status data for a plurality of electric field detectors. For each electric field detector, the status data may include data indicative of an identity of the electric field detector, a geographic location of the electric field detector, an indication of whether the electric field detector is alarming (i.e., the electric field detector has detected a high-voltage power source), and/or a timestamp associated with the status data.

On a given data terminal, such as a smartphone, a tablet computer, a laptop computer, or a desktop computer, a user may cause the device to run a detector monitoring client program, and the central computer may responsively cause a display component of the data terminal to display a graphical user interface. Displaying the graphical user interface may include presenting indicia of the status data for one or more electric field detectors. For each electric field detector, the presented indicia may include an icon or graphic and/or text indicative of the location of the electric field detector, the alarm state of the electric field detector (i.e., whether the electric field detector is alarming in response to detecting a high-voltage power source), the identity of the electric field detector or user of the electric field detector, and/or a timestamp associated with such data.

The central computer may periodically receive updates to the status data for each of the one or more electric field detectors. Responsive to receiving such data for a given electric field detector, the central computer may automatically transmit to the data terminal data for updating the indicia of the status data for the electric field detector. Advantageously, the user can thus monitor multiple electric field detectors in a variety of geographic locations. For example, a supervisor remotely supervising repairs to high-voltage transmission lines following a storm may be able to monitor multiple worksites, thereby allowing the supervisor to quickly identify potentially dangerous situations to workers and to responsively take appropriate action to minimize the risk of injury to those workers. Being able to quickly identify the approximate locations of live high-voltage power sources may also assist the supervisor in coordinating repair or maintenance efforts.

A user may also interact with the graphical user interface to select a subset of electric field detectors to monitor for detection of a high-voltage power source. Upon receiving data indicative of such selections, the central computer may cause the display component to present indicia of the status data of each electric field detector included in the subset of electric field detectors while removing the indicia of the status data of all other electric field detectors. In this manner, the graphical user interface may allow the user to monitor specific electric field detectors, such as one or more electric field detectors located at a particular worksite or in a particular geographic area.

As an additional safety feature, the central computer may cause one or more data terminals running the detector monitoring client program data to provide a visual output (e.g., a message box displayed on the graphical user interface), an audible output (e.g., a unique tone, sequence of tone, or other sound), and/or a tactile output (e.g., a vibration or sequence of vibrations) upon determining that a nearby electric field detector has detected a high-voltage power source. The one or more data terminals may include data terminals located in the vicinity of the electric field detector, such as smartphones of workers, and/or data terminals configured to remotely monitor the alarming electric field detector. The provided output or outputs may thus alert a worker in the field of potentially hazardous condition, and may further notify a supervisor remotely monitoring the worksite of the location of a live high-voltage power source.

As a general matter, the central computer can be implemented as a cloud-based computing system or as a single computing device. When implemented as a cloud-based computing system, the central computer may comprise a plurality of remote servers or server clusters configured to distribute execution of the detector monitoring program to provide the graphical user interface. As such, the central computer may receive status data for electrical field detectors located in a number of geographic areas, and a plurality of data terminals located in a plurality of geographic areas may similarly connect to the central computer in order to receive the graphical user interface.

In this implementation, each electric field detector and each data terminal may be associated with one (or possibly more than one) account. When providing the graphical user interface to a data terminal, the central computer may present indicia of the status data for each electric field detector associated with the same client account as the data terminal.

On the other hand, a single computing device implementation of the central computer may be directly configured to provide the graphical user interface and alerts to data terminals located in a smaller geographic area, as compared to the cloud-based computing system implementation. Here, the data terminal, which could include an electric field detector itself, may communicate directly with the central computer. As one example, the central computer may provide a WIFI hotspot to which data terminals and/or electric field detectors within a limited distance from the central computer may connect. Alternatively, the data terminals and/or electric field detectors may connect to the central computer via a different medium.

In the single computing device implementation, the detector monitoring program running on the central computer would receive the status data for each locally located electric field detector, perhaps directly, and then self-generate the graphical user interface. Further, the central computer in this implementation may be configured to connect to a server or cloud-based computing system in order to provide remote monitoring.

For simplicity of illustration and explanation, the present disclosure will focus primarily on the cloud-based computing system implementation from this point forward. However, it should be noted that the disclosure is not restricted to that implementation and that the functions described herein can be applied by analogy to the single computing device system implementation and in other implementations, such as hybrid implementations of the cloud-based computing system and the single computing device system.

Referring now to the drawings, FIG. 1 is a simplified block diagram of an example system 10 in which features of the present mechanism can be implemented. In particular, the system 10 includes a plurality of electric field detectors 12, a plurality of local data terminals 14, a plurality of remote data terminals 16, network 18, and server 20.

As shown in FIG. 1, each electric field detector 12 is coupled to one of local data terminals 14. As noted above, local data terminals 14 may include, without limitation, smartphones, tablet computers, mobile phones, notebook computers, media players, and/or other, preferably (but not necessarily) portable, electronic devices.

In one example, each electric field detector 12 and respective local data terminal 14 communicate via a short-range wireless link, such as a BLUETOOTH® link, as indicated in FIG. 1 by a dashed line. In another example, the short-range wireless link conforms to a different standardized or proprietary protocol. And in still other examples, a given electric field detector 12 may communicate via a wired link with a respective local data terminal 14.

Local data terminals 14 are also connected to network 18, as are remote data terminals 16 and server 20. Preferably, local data terminals 14 connect to network 18 through a cellular wide area network connection, such a through a cellular service provider's radio access network. In other examples, local data terminals 14 may connect to network 18 via a different wireless connection, such as WIFI network.

On the other hand, remote data terminals 16 and server 20 may each connect to network 18 via a wireless and/or wired connection. As such, remote data terminals 16 may include, without limitation, desktop computers, smartphones, tablet computers, mobile phones, notebook computers, media players, and security systems.

Network 18 may be, for example, the Internet, or some other form of public or private Internet Protocol (IP) network. Thus, local data terminals 14, remote data terminals 16, and server 20 may communicate using packet-switching technologies. In some examples, however, network 18 may also incorporate at least some circuit-switching technologies, in which case local data terminals 14, remote data terminals 16, and server 20 communicate via circuit switching alternatively or in addition to packet switching.

Further, application-level communications between devices on network 18 may be carried out according to any agreed protocol. By way of example, nodes may communicate with each other according to the Hypertext Transfer Protocol (HTTP) or Session Initiation Protocol (SIP), or using more advanced interactive web applications such as Asynchronous JAVASCRIPT and XML (AJAX), each of which is well known and therefore not described here. Numerous other examples may be possible as well.

Figure 2:
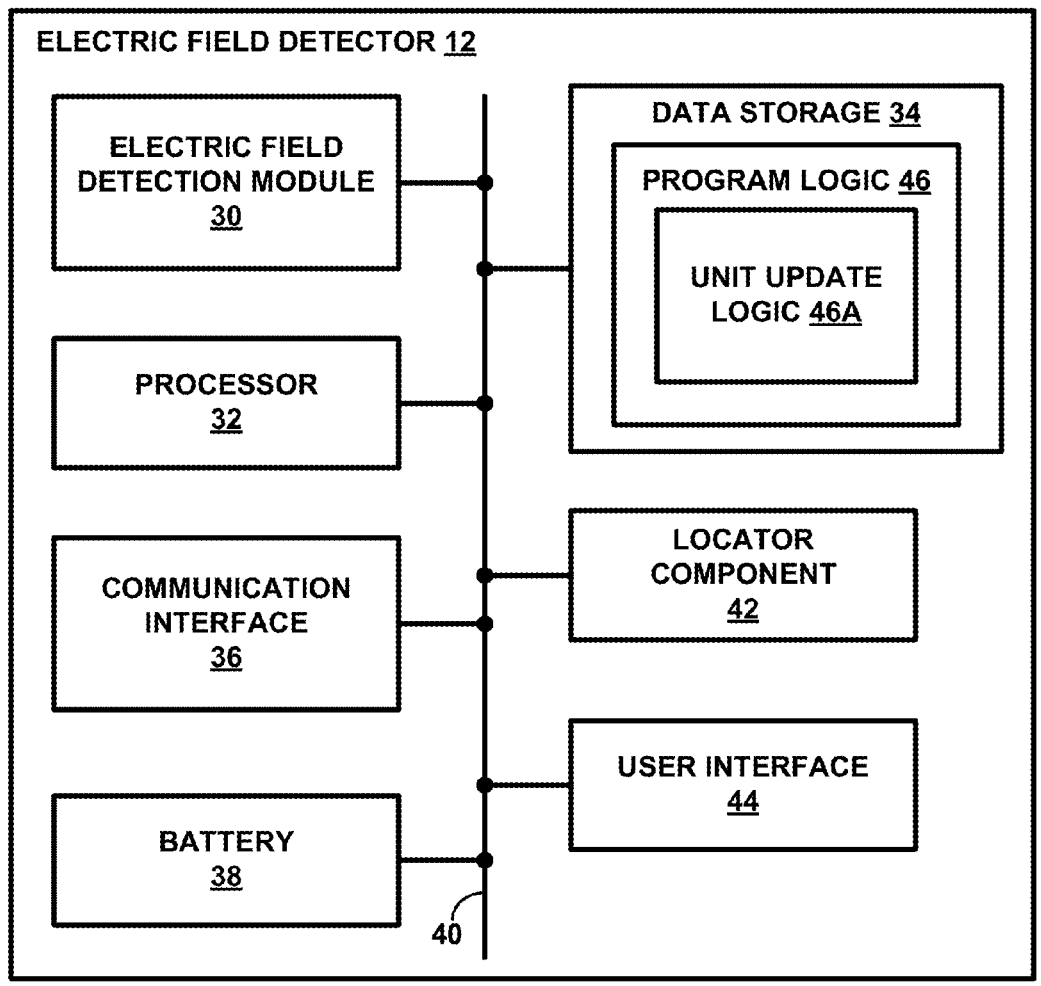
FIG. 2 is a simplified block diagram of an electric field detector, according to an example.

FIG. 2 is a generalized block diagram depicting functional components of an example electric field detector 12. As shown, the example electric field detector 12 includes electric field detection module 30, a controller 32, data storage 34, communication interface 36, and battery 38, all of which may be coupled together by a system bus, network, or other connection mechanism 40. Additionally, in some examples, such as a single computing device implementation of system 10, electric field detector 12 may include optional locator component 42 and user interface 44.

Electric field detector 12 may take various forms. In one example, electric field detector 12 comprises a single, waterproof housing that can be worn by a user, e.g. a utility worker in the field. Electric field detector 12 may also have two means for securing the electric field detector to the user's body, such as a lanyard and a tension clip. In some embodiments, the electric field detector 12 does not have an on/off switch and is thus always on while the battery 36 is connected.

By way of example, electric field detector 12 may be configured to detect 16$w$-frequency fields of the type which surround high-voltage conductors, such as power transmission and distribution lines and equipment. Thus, the electric field detection module 30 may detect electric fields having a frequency within a range of about 50 Hertz to about 60 Hertz.

In other examples, electric field detector 12 may be configured to detect electric fields at different frequencies. For instance, the electric field detection module 30 may be configured to detect electric fields having frequencies as low as about 25 Hertz, which may be useful in applications in which a user of electric field detector 12 is working in the vicinity of electrified train rails.

Electric field detection module 30 may thus include components and circuitry for detecting an electric field and to provide one or more alarms when a magnitude of a detected electric field exceeds at least one threshold magnitude. For instance, electric field detection module 30 may include one or more electrodes configured to sense an electric field, circuitry to determine whether a magnitude of a detected electric field exceeds at least one threshold, and one more output components for providing an alarm. One such example of the components and electrical circuitry of electric field detection module 30 is disclosed in U.S. Pat. No. 6,329,924, which issued on Dec. 11, 2001, the contents of which are hereby incorporated by reference.

Electric field detection module 30 provides one or more alarms when a magnitude of a detected electric field exceeds each of three threshold magnitudes. For instance, electric field detection module 30 may provide a first set of alarms when the magnitude of the electric field exceeds a first threshold magnitude, a second set of alarms when the magnitude of the electric field exceeds the second threshold magnitude, and a third set of alarms when the magnitude of the electric field exceeds a third threshold magnitude.

The output components of electric field detection module 30 may take any number of forms. For instance, the electric field detection module 30 may include a speaker, one or more light emitting diodes (LEDs), and/or a tactile-output generator. In this example, the first set of alarms may include slowly flashing one or more LEDs, slow intermittent beeps, and/or a low-intensity vibration; the second set of alarms may include quickly flashing the one or more LEDs, fast intermittent beeps, and/or a medium-intensity vibration; and the third set of alarms may include continuously lighting the one or more LEDs, a continuous tone, and/or a high-intensity vibration.

Optional locator component 42 may comprise one or more receivers (or transceivers), such as a navigation system receiver, arranged to receive signals usable by electric field detector 12 to facilitate determination of the location of electric field detector 12. Locator component 42 may be included in embodiments of electric field detector 12 in which electric field detector 12 is configured to directly connect to network 18. By way of example, locator component 42 may include one or more receivers configured for use with a navigation system, such as Global Positioning System (GPS), Global Navigation Satellite System (GLONASS), BeiDou/COMPASS, Doppler Orbitography and Radio-positioning Integrated by Satellite (DORIS), Galileo, and/or the like. Location determination may be carried out by electric field detector 12 itself or possibly with assistance of a location-determination server or a positioning system accessible via network 18.

Controller 32 may include one or more general purpose processors (e.g., microprocessors) and/or one or more special purpose processors (e.g., application specific integrated circuits and/or digital signal processors). Data storage 34 may then comprise one or more volatile or non-volatile, non-transitory storage components such as magnetic, optical, organic, or solid state (e.g., flash) storage components, and may be wholly or partially integrated with controller 32.

As shown, data storage 34 contains program logic 46 executable by the controller 32 to carry out various functions described herein. Specifically, program logic 46 may include unit update logic 46A, which may function (i) to periodically generate and transmit a heartbeat signal, (ii) determine and store in the data storage data indicative of a current alarm state (i.e., which magnitude threshold, if any, is currently exceeded), and (iii) to generate and transmit or to cause controller 32 to generate and transmit an alarm signal in response to electric field detection module 30 detecting an electric field having a magnitude that exceeds at least one threshold magnitude.

Generally speaking, the heartbeat signal provides an indication of the electric field detector being coupled to one of local data terminals 14. Additionally, the heartbeat signal may include data indicative of a current status of battery 38 and the current alarm state. To this end, unit update logic 46A may further function (i) to determine the current charge level of battery 38, (ii) to determine whether the current charge level of the battery is less than or equal to a threshold level, and (iii) to include in the heartbeat signal data indicative of the determined current charge.

To generate the alarm signal, unit logic 46A may further function to include in the alarm signal data indicative of the threshold magnitude that the magnitude of the electric field exceeded, or perhaps a measured magnitude of the electric field if the electric field detection module is so configured to measure the magnitude.

In examples in which the electric field detector 12 includes locator component 42, the unit update logic 46A may further include instructions (i) for using locator component 42 to determine a location of electric field detector 12 and (ii) to transmit data indicative of the determined location.

Network communication interface 36 may provide for wired and/or wireless communication with a data terminal. By way of example, network communication interface 36 may include a module for engaging in short-range wireless communication with a data terminal. If the data terminal is one of local data terminals 14, then the short-range wireless communication is preferably a low-power short-range communication protocol, such as BLUETOOTH® communication (e.g., standard BLUETOOTH® and/or BLUETOOTH® Low Energy), Zigbee, and/or other short-range wireless communication protocol. In these examples, a transmission range of network communication interface 36 may be about one meter.

Additionally or alternatively, network communication interface module 36 may include a module for engaging in a comparatively longer-ranged communication protocol, such as WIFI. In these examples, the transmission range of network communication interface 36 may be between about one meter and about one hundred meters.

And in other examples, the network communication interface 36 may include a module for wired communication, such as USB connection, with one of local data terminals 14.

In examples in which electric field detector 12 is configured to connect directly to a central computer in a detector monitoring system, electric field detector 12 may include the optional user interface 44. User interface 44 includes input components and output components to facilitate establishing a communication link between the electric field detector and another device. User interface 44 may thus include input components such as a keyboard, keypad, pointing device, touch-sensitive display screen, microphone, and video camera, among others. User interface 44 may further include a display device, such as a liquid crystal display (LCD) or an LED display, among other examples.

Figure 3:
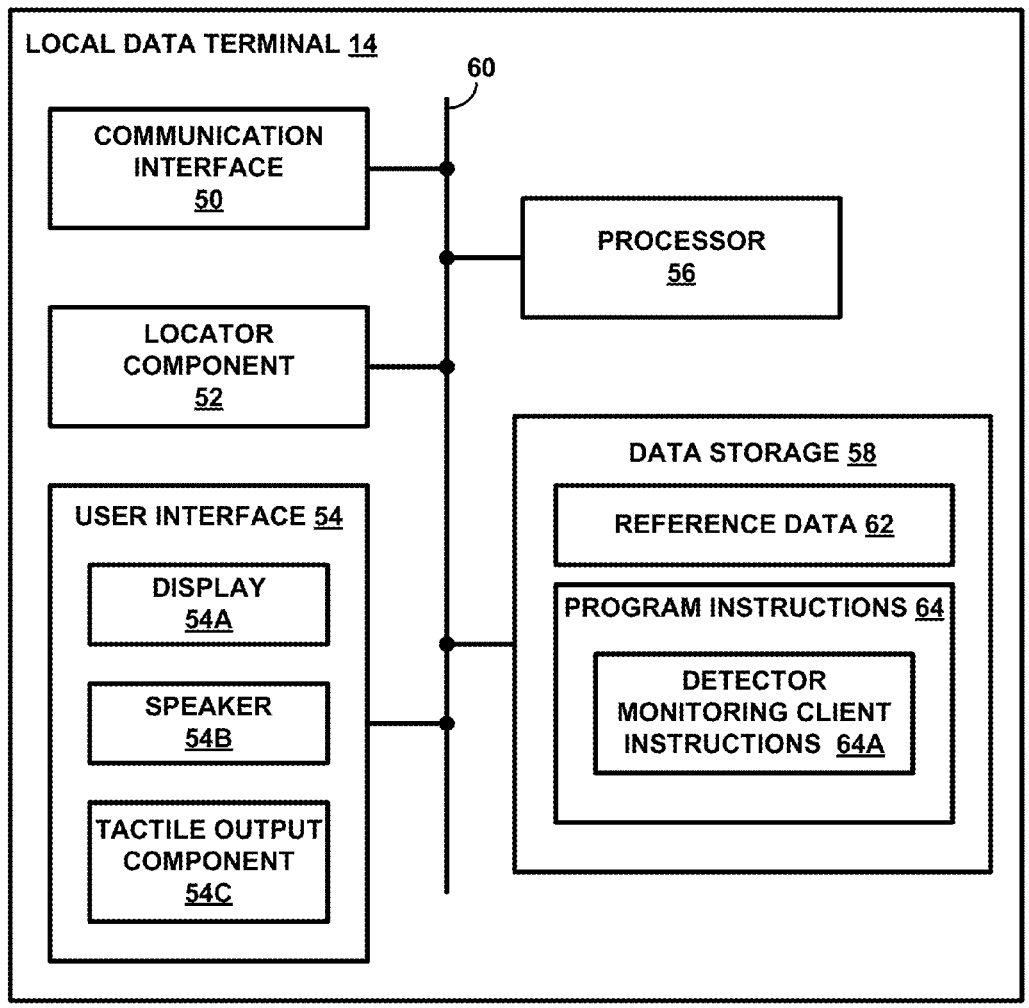
FIG. 3 is a simplified block diagram of a data terminal, according to an example.

Now turning to FIG. 3, a generalized block diagram is shown depicting functional components of local data terminal 14. Specifically, local data terminal 14 includes network communication interface 50, locator component 52, user interface 54, processor 56, and data storage 58, all of which may be coupled together by a system bus, network, or other connection mechanism 60.

Network communication interface 50 may provide for wired and/or wireless communication in a personal area network, local area network, metropolitan area network, wide area network, or any other type of network. In line with the above discussion, network communication interface 50 may include a module for engaging in short-range wireless communication (e.g. BLUETOOTH® communication), with one of electric field detectors 12. As another example, network communication interface 50 may include a module for engaging in wired communication with one of electric field detector 12, perhaps in the form of a USB connection. Additionally, network communication interface 50 may include a module for engaging in cellular wide area network communication, such as through a cellular service provider's radio access network for instance Locator component 52 may comprise a navigation system receiver, such as a standard GPS receiver, arranged to receive signals usable to facilitate determination of the location of local data terminal 14 and, by extension, a communicatively coupled electric field detector. By way of example, locator component may include one or more receivers configured for use with a navigation system, such as GPS, GLONASS, BeiDou/COMPASS, Doppler Orbitography and Radio-positioning integrated by Satellite (DORIS), Galileo, and/or the like. Location determination may be carried out by local data terminal 14 itself or possibly with assistance of a location-determination server or a positioning system accessible via network 18.

User interface 54 functions to facilitate device interaction with a user and may thus take various forms. By way of example, user interface 54 may include output components such as display 54A for providing visual output, speaker 54B (which may include a headset connection) for providing audible output, tactile output component 54C for providing tactile output (e.g., vibration), among others. Further, user interface 54 may include input components 54D such as a keyboard, keypad, pointing device, touch-sensitive display screen, microphone, and video camera, among others.

Processor 56 may comprise one or more general purpose processors (e.g., microprocessors) and/or one or more special purpose processors (e.g., application specific integrated circuits and/or digital signal processors). Data storage 58 may then comprise one more volatile or non-volatile, non-transitory storage components such as magnetic, optical, organic, or solid state (e.g., flash) storage components, and may be wholly or partially integrated with processor 56.

As shown, data storage 58 is arranged to include reference data 62, and further contains program instructions 64 executable by processor 56 to carry out various data terminal functions described herein. For instance, as shown, program instructions 64 may include detector monitoring client instructions 64A, which may function (i) to cause the local data terminal 14 to receive a heartbeat signal or an alarm signal from an associated electric field detector 12, (ii) to determine a location of the local data terminal 14, (iii) to generate a status signal that includes status data for the associated electric field detector, and (iv) to transmit the status signal to server 20 for processing.

Further, if and when local data terminal 14 functions as a device whose display will present the graphical user interface of the detector monitoring system, detector monitoring client instructions 64A may further function (i) to receive the graphical user interface from server 20, (ii) to present the graphical user interface, (iii) to receive user input provided through the graphical user interface, and (iv) to transmit data corresponding to that received input to server 20.

Reference data 62 may include a time log of each position and alarm state of associated electric field detector 12. A timestamp associated with each such position and alarm could be either a time at which local data terminal 14 received the unit signal from associated electric field detector 12 or a time which processor 56 determined the position of the local data terminal 14. Alternatively, such a data log could be stored in server 20, which may be the case in a cloud-based implementation of the detector monitoring system.

It should be noted that remote data terminals 16, as described with respect to FIG. 1, may include the same or substantially similar components as the local data terminal 14 described with respect to FIG. 3. In operation, however, remote data terminals 16 may not be communicatively coupled to an associated electric field detector 12.

Alternatively, one or more remote data terminals 16 may be communicatively coupled to an electric field detector that is not part of the monitored group of electric field detectors. In this manner, a user of such remote data terminal 16 may remotely monitor electric field detectors 12 in one worksite while being physically located in another worksite.

Figure 4:
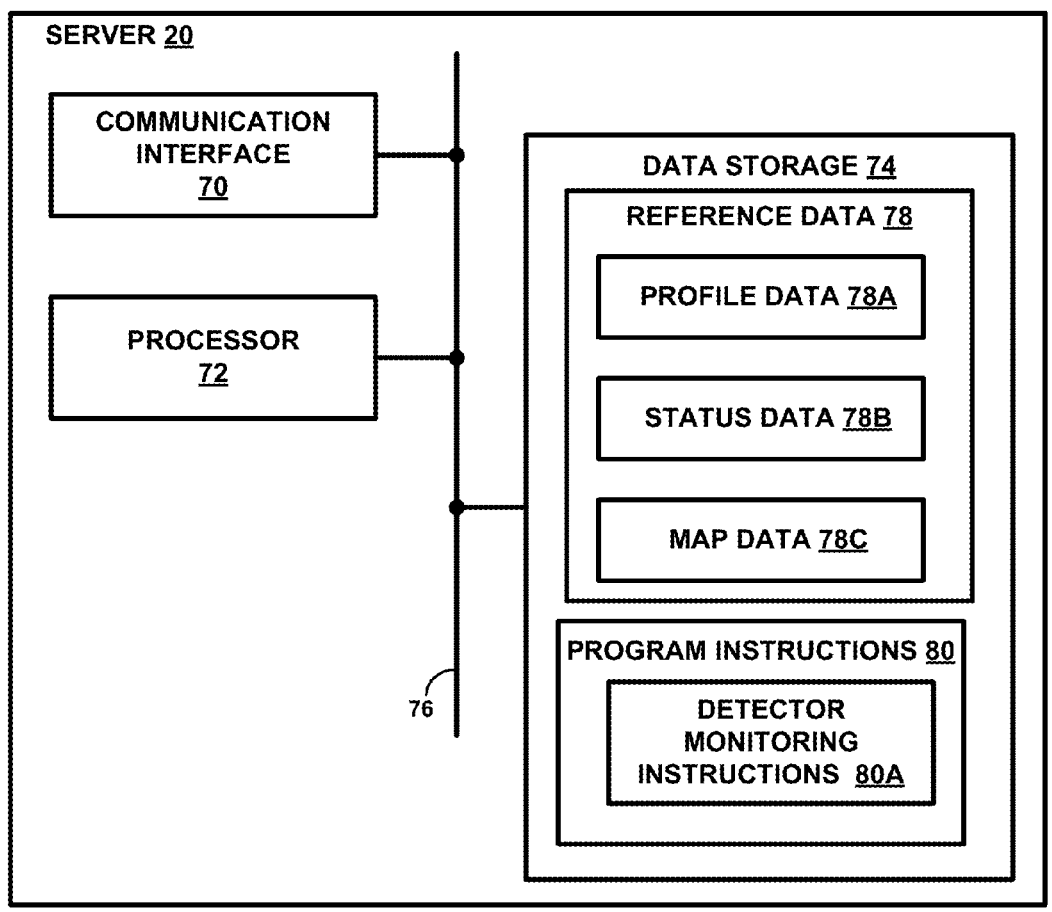
FIG. 4 is a simplified block of a server, according to an example.

FIG. 4 is a simplified block diagram depicting functional components of server 20. For simplicity, FIG. 4 does not depict a cluster-based computing environment, but server 20 could be implemented as such. As shown in FIG. 4, server 20 includes network communication interface 70, processor 72, and data storage 74, all of which may be coupled together by a system bus, network, or other connection mechanism 76.

Network communication interface 70 may comprise any module that enables server 20 to communicate on network 18, so as to facilitate communicating with local data terminals 14, remote terminal 16, and, in some embodiments, electric field detectors 12. By way of example, network communication interface 70 may be a wired or wireless Ethernet network interface, coupled by one or more routers or other connection devices with network 18.

Processor 72 may comprise one or more general purpose processors (e.g., microprocessors) and/or one or more special purpose processors (e.g., application-specific integrated circuits and/or digital signal processors). Data storage 74 may then comprise one or more volatile or non-volatile, non-transitory storage components such as magnetic, optical, organic, or solid state (e.g., flash) storage components, and may be wholly or partially integrated with processor 72.

As shown, data storage 74 is arranged to hold reference data 78 and program instructions 80. In practice, reference data 76 may include user profile data 76A, status data 76B, and map data 76C. Program instructions 80 may then include program instructions (e.g., machine language instructions) executable by processor 72 to carry out various central computer functions described herein, particularly to facilitate the various detector monitoring functions for one or more users.

In practice, it will be understood that data storage 74 thus represents an example of a non-transitory computer-readable medium having stored thereon instructions executable by a computing system to carry out various panel-management functions described herein. However, in other implementations, the non-transitory computer-readable medium containing such instructions could take various other forms, such as a CD-ROM, a DVD-ROM, a magnetic disk drive, or other removable or non-removable, non-transitory computer readable medium.

User profile data 76A may include user profiles for various users or groups of users who have a detector monitoring account or who have an account for a service that also provides for detector monitoring. As such, user profile data 76A may identify each user or group by a user name or other unique identifier. Server 20 may make use of user profile data 76A to authorize users seeking to use the detector monitoring service.

Additionally, for each worker who wears an electric field detector, the worker's user profile may be associated with the worker's electric field detector. User profile data 76A may thus include information for identifying the user of a particular electric field detector, which server 20 may access when generating the graphical user interface for detector monitoring.

Further, user profile data 76A may include data indicative of a plurality of one or more electric field detectors that are associated with a given user profile. For example, a user profile stored in the user profile data 76A may be associated with a serial/identification number or other unique identifier associated for each of one or more electric field detectors. Server 20 may thus use the user profile to identify the electric field detectors that the user can monitor.

Status data 76B may include one or more sets of status data for each of electric field detector 12. As previously discussed, each set of status data for a given electric field detector 12 may include a serial/identification number of the electric field detector, a position of the electric field detector, an alarm state of the electric field detector, a battery level of the electric field detector, and a timestamp. In other examples, each set of status data could include more, less, and/or different data.

As noted above, status data 76B may include multiple sets of status data for each electric field detector. To this end, the most recent status data for a given electric field detector, e.g., the status data with the most recent timestamp, may be stored in position data 76B as a current set of status data. Server 20 may thus access the status data 76B to identify the current set of status data when generating the graphical user interface for a given user.

Status data 76B may also include one or more historical sets of status data for one or more electric field detectors, e.g., sets of status data other than the current set of status data. The number of historical sets of status data may be determined by a user profile manager, and in some examples status data 76B may not include any historical sets of status data. In one example, server 20 may access status data 76B when generating a graphical user interface that presents a log of status data, thereby allowing a user to review historical trends in status data based on status data for a particular device or geographic location or area.

Map data 76C may include data for displaying each of a plurality of maps for each of one or more geographic areas. Server 20 may access map data 76C when generating the graphical user interface. For instance, server 20 may generate a graphical user interface that includes an indicium representative of a location of each of one or more electric field detectors, with such indicia overlaid on a map at positions corresponding to the positions of the electric field detectors.

Server 20 may also access map data 76C to determine a geographic location of an electric field detector based on received status data for that electric field detector. For example, if the received status data for the electric field detector is in the form of geographic coordinates, server 20 may use the coordinates and the map data 76C to determine a street address or intersection corresponding to the coordinates, which may then be stored in status data 76B.

Server 20 may also access map data 76C after receiving an alarm signal in order to identify electric field detectors located in the vicinity of an alarming electric field detector. Server 20 may, for example, use map data 76C and status data 76B to identify any electric field detectors 12 that are within a radius of the alarming electric field detector. In one example, the radius may be approximately 100 yards, though the radius could be larger or smaller depending on the application and/or the user's preferences.

Although FIG. 4 shows the data storage 76 storing map data 76C, the map data 76C could be stored in a separate data storage accessible by server 20. In that arrangement, server 20 may regularly access the separate data storage to access the requisite map data needed to present a data terminal with a graphical user interface.

Additionally or alternatively, server 20 may acquire from a third-party server map data needed to provide the graphical user interface and temporarily store such map data in map storage 76C. Once the graphical user interface is no longer needed (i.e., no users running the graphical user interface component of the detector monitoring program), server 20 may remove the map data. In this manner, the size of map data 76C may be reduced as compared to an example in which all map data 76C is permanently stored in data storage 76 and/or a separate data storage unit.

Detector monitoring instructions 80A may executable by processor 72 to provide aspects of a graphical user interface to a data terminal, such as one of local data terminals 14 and/or remote data terminals 16. For instance, detector monitoring instructions 64A may function (i) to provide the data terminal with a graphical user interface that presents indicia of status data for one or more electric field detectors, (ii) cause the data terminal to update the presented indicia based on updated status data for one or more of the electric field detectors, (iii) receive from the data terminal data corresponding to a user input, (iv) determine an update to the presented indicia based on the user input, and (v) provide the data terminal with an updated graphical user interface and/or data for updating the presented indicia.

In an example in which instructions for presenting the graphical user interface are stored in the data terminal, the detector monitoring instructions 80A may function to (i) receive from the data terminal data corresponding to a selection of one or more electric field detectors, (ii) provide to the data terminal status data for one or more electric field detectors, and (iii) provide to the data terminal updated status data for the one or more electric field detectors.

In practice, server 20 functions to receive status data from one or more electric field detectors 12 via one or more local data terminals and to provide a graphical user interface that presents indicia of the status data on a display. FIGS. 5A-5E are a series of images representing conceptually how this graphical user interface may look and operate in an example implementation. As with other descriptions throughout this document, it should be understood that many variations from this example are possible.

Each of FIGS. 5A-5E presents an image representing a display presented on a display component of a data terminal, such as a smartphone, a tablet computer, a notebook computer, or a desktop computer, among others. Due to the limited display space on such a device, it may not be possible for the display to show the entire graphical user interface at once. Rather, the display may present certain aspects of the graphical user interface in a scrollable or moveable manner, and the display may present individual various aspects of the graphical user interface in the form of separate display windows, tabs, panes, cards, or the like. Alternatively, it is of course possible that more of the graphical user interface may be presented at once, such as by concurrently various sections of the type shown in the figures.

Optimally, much of the display in the example graphical user interface will be communicated dynamically (e.g., asynchronously) between a data terminal and server 20. For instance, upon initial request from the data terminal, server 20 may transmit a first display page to the device to cause the device to present the page, and the device may responsively present that page on its display. While the page is displayed, the data terminal may then receive user input such as the user clicking on or otherwise selecting a specific portion of the page, and the data terminal may responsively transmit to server 20 data corresponding to that user input. In response to receiving such data, or at any other time while the page is being displayed, server 20 may then transmit to the data terminal some updated content for the page, and the data terminal may responsively present that updated content in the currently presented page, so as to dynamically (e.g., asynchronously) update the presented content.

For example, server 20 may transmit to the data terminal a page that presents indicia of the status data for each of a plurality of electric field detectors, and the data terminal may responsively present that page on its display. As server 20 receives additional status data for the displayed electric field detectors, server 20 may then transmit to the device data that represents an update of the currently displayed page, such as to replace currently displayed indicia with other indicia, or to add new indicia of the status data to the display. As noted above, an interactive web application technology, such as AJAX, could be used for this purpose.

Further, to allow the server to programmatically determine when the data terminal is presenting a given page, such as a display of indicia of status data positioned on a map, the data terminal may be arranged to transmit a signal to server 20 when the device closes or is otherwise not displaying the page. Alternatively, the data terminal may transmit periodic signals to server 20 while the page is actively displayed, and sever 20 may programmatically determine that the data terminal is not being displayed when such a signal is not received within a given period of time.

When a user of a data terminal first calls-up the detector monitoring program, the user may select from one of two components of the graphical user interface: a map component or a list component. As used herein, a "component" of the graphical user interface, may be a discrete portion of the graphical user interface, such as a separate window for instance, or may be a functional aspect of the graphical user interface that is not limited to discrete presentation. For instance, a given component that functions to present particular elements may also be used as part of another component that presents the same particular elements.

Figure 5A:
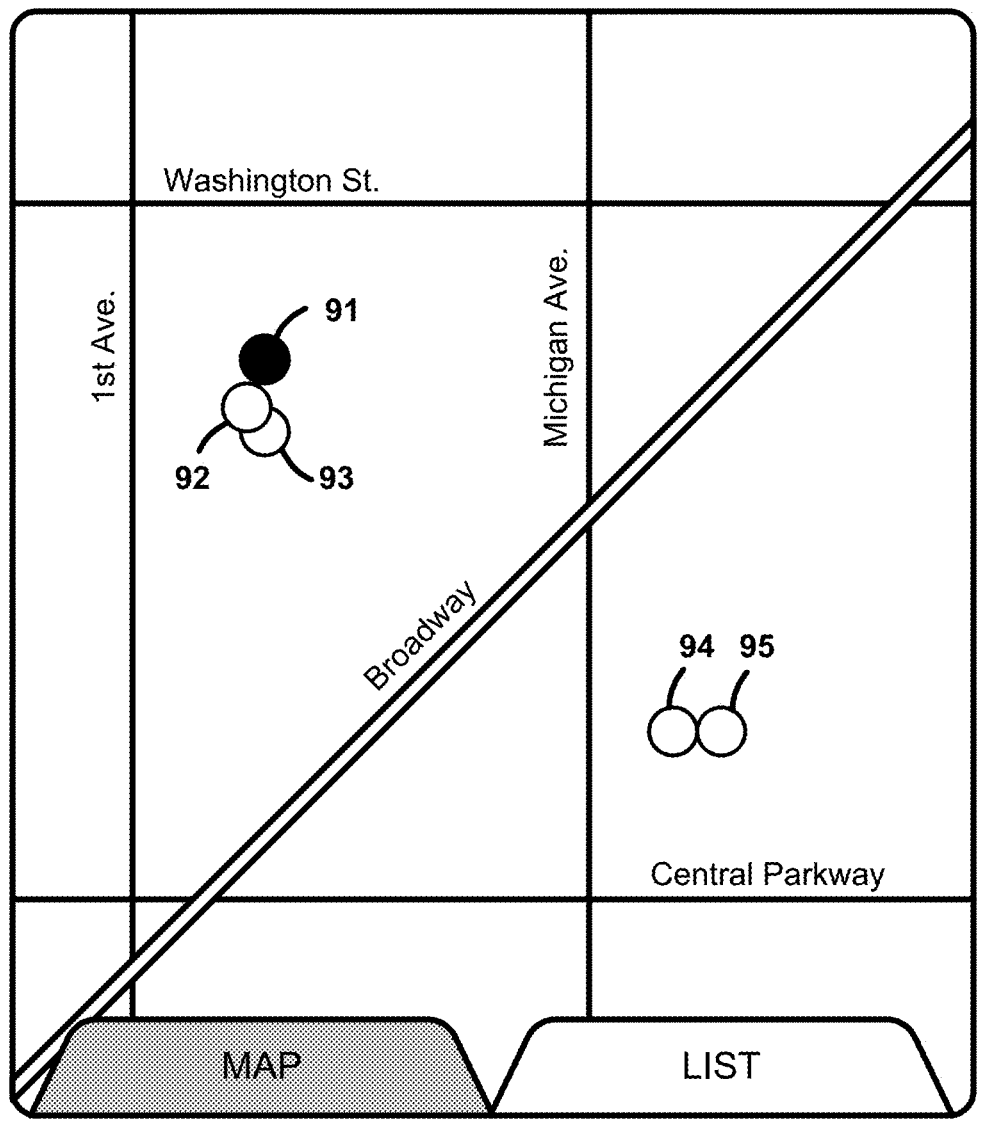

When the user selects the map component, server 20 (or perhaps another entity connected to network 18) may provide the user's data terminal with a map display, as shown in FIG. 5A. The map display includes a presentation of a map of a geographic area in which electric field detectors associated with the user's profile are located. The map display may present indicia of the alarm states for each such electric field detector, with each indicium being presented on the map at a position that reflect the geographic location of the associated electric field detector and indicates an alarm state of the associated electric field detector. In the illustrated examples described herein, for example, a first indicium 91 corresponds to a first electric field detector, a second indicium 92 corresponds to a second electric field detector, a third indicium 93 corresponds to a third electric field detector, a fourth indicium 94 corresponds to a fourth electric field detector, and a fifth indicium 95 corresponds to a fifth electric field detector.

Server 20 may receive updated status data for the monitored electric field detectors, and server 20 may then update the indicia and/or the position of the indicia on the map, thereby presenting the user with real-time or nearly real-time changes in the alarm state and/or position of the monitored electric field detectors.

In the example depicted herein, the presented indicia of the status data include graphical icons in the form of colored circles, with each color corresponding to a particular alarm state. By way of example, Table 1 shows one possible correspondence of the color of each icon to an alarm state of an associated electric field detector:

TABLE 1

| Color | Alarm State |
| --- | --- |
| First Color | Alarm State 0 |
| Second Color | Alarm State 1 |
| Third Color | Alarm State 2 |
| Fourth Color | Alarm State 3 |

As a further example, the first color may be green, the second color may be yellow, the third color may be orange, and the fourth color may be red. In other examples, more, fewer, and/or different colors may be used to represent a particular alarm state. Additionally or alternatively, the presented indicia of the alarm states may take any number of forms, such as a different geometric shape or a graphical representation of an object.

Figure 5B:
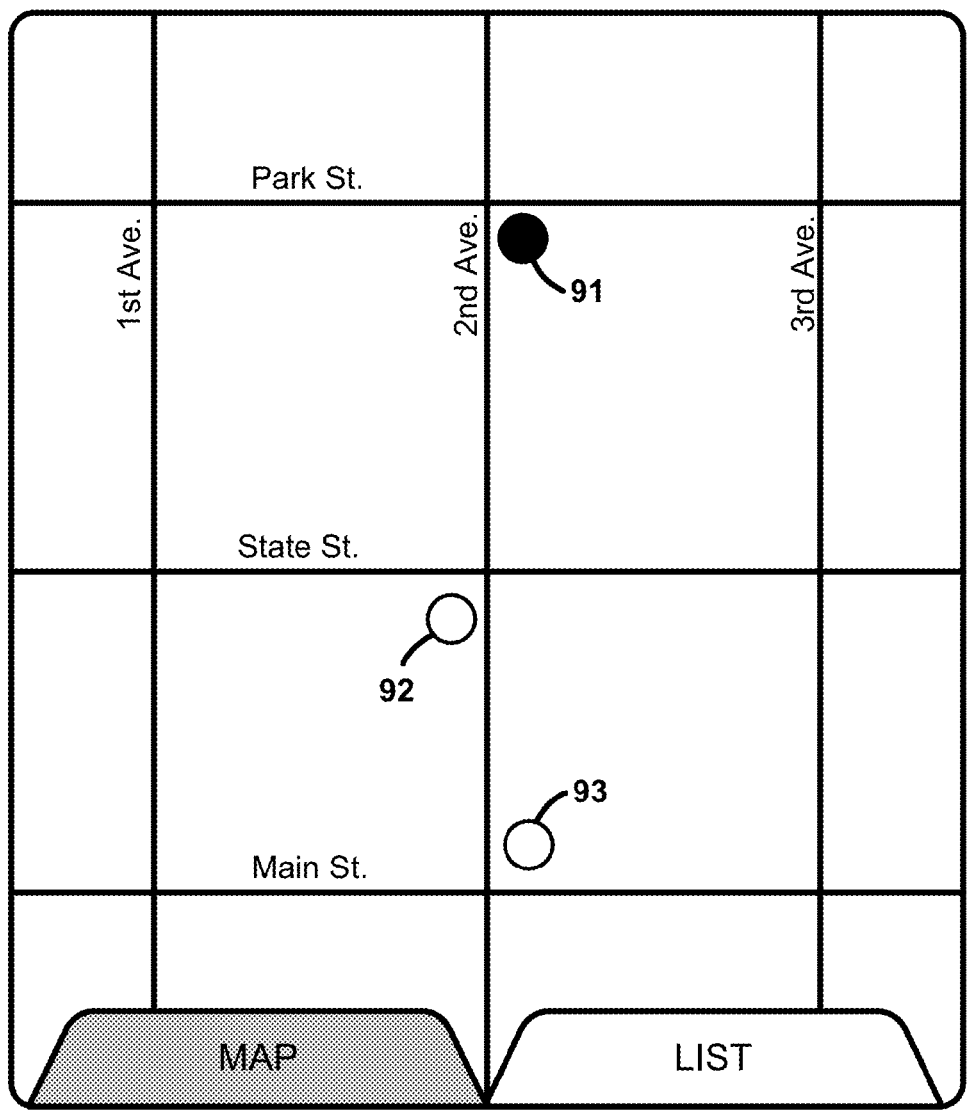

In operation, the user may interact with the graphical user interface to focus on a particular area, such as a worksite in which an electric field detector has alarmed as shown in FIG. 5B. To this end, the user may interact with graphical user interface to zoom in on a particular area of the map, thereby selecting a map area. The data terminal may send to server 20 information data corresponding to the selected area, and server 20 may responsively update the map display to show the indicia of the alarm state of the electric field detectors in the selected area. The user may similarly interact with the graphical user interface to zoom out on the map, thereby causing the display to present indicia of the status data for additional electric field detectors.

Alternatively, the user may interact with the graphical user interface to monitor a subset of electric field detectors. Upon receiving data corresponding to such input, server 20 may filter the map display to remove the presented indicia of the status data for each electric field detector not included in the subset of electric field detectors. The server may also automatically rescale the map display such that the map has a minimum scale for presenting the indicia of the status data for each electric field detector in the subset of electric field detectors.

FIG. 5B shows three indicia of the status data, with indicium of status data 91 corresponding to a first electric field detector, indicium of status data 92 corresponding to a second electric field detector, and indicium of status data 93 corresponding to a third electric field detector.

The user may interact with the graphical user interface to select a presented indicium. By way of example, the data terminal may transmit to sever 20 data indicative of the user selecting indicium of status data 91, and server 20 may responsively send to the data terminal data for presenting the display shown in FIG. 5C. In this example, the map display includes a presentation of message window 90, which provides additional indicia of the status data for the first electric field detector. Such additional indicia can include a name of the worker wearing the first electric field detector, a serial number of the first electric field detector, timestamp information corresponding to the status data (e.g., a time at which the position was determined or a time at which the status data was generated), location information (e.g., a street address), and/or a phone number or other means to contact the user. In other examples, the additional indicia may include more, fewer, and/or different data.

Figure 5C:
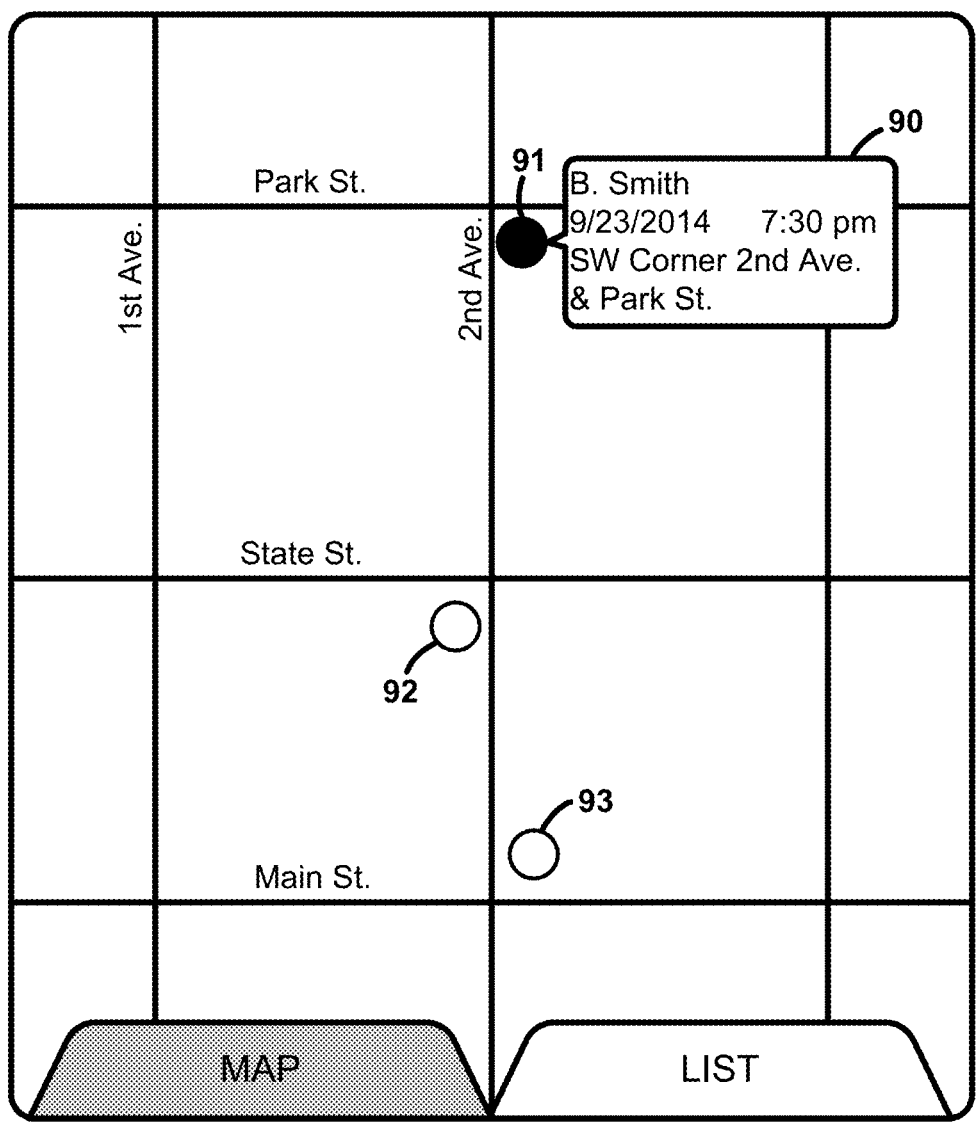

As shown in FIGS. 5A, 5B, and 5C, indicium of status data 91 is indicative of the first electric field detector alarming, indicating that the user of that electric field detector is in relatively close proximity to a high-voltage power source. Advantageously, identifying the location of the first electric field detector, and thus the worker who is in relatively close proximity to a high-voltage power source, may allow the user to coordinate repair and/or maintenance efforts by directing another worker to the location of the high-voltage power source. Remote identification of the high-voltage power source may also assist the user in determining how to deactivate electrical equipment supplying the high-voltage power source while minimizing disruption of electrical services to consumers in the area.

As a further benefit, identifying the name of the worker using the first electric field detector and/or the serial/identification number of the electric field detector may allow assist the user in expeditiously contacting the worker to receive an on-the-ground assessment of the situation. In some examples, the phone number associated with the worker may be displayed or be selectable in message window 90, and the user can then interact with the graphical user interface to call the worker.

To continue the illustrative example, the user may direct the worker wearing the second electric field detector to the location of the first electric field detector. As that worker nears the vicinity of the first electric field detector, the second electric field detector may also alarm. This, in turn, may cause the second electric field detector to send an alarm signal to a communicatively coupled local data terminal (e.g., smartphone running the detector monitoring client program), which responsively generates and transmits to server 20 an alarm signal.

Server 20 may then process the alarm signal and determine that the alarm signal includes information indicative of an alarm condition. Server 20 may responsively identify one or more electric field detectors that are within a range of the second electric field detector, and server 20 may then send an alert signal to a data terminal communicatively coupled to each identified electric field detector. In the illustrated example, for instance, server 20 may send the alert signal to a data terminal communicatively coupled to each of the first electric field detector and the third electric field detector.

In one example, however, server 20 may not send the alert signal to a local data terminal that is communicatively coupled to an alarming electric field detector. Thus, in an example in which the first electric field detector and third electric field detector are each within the range of the second electric field detector, server 20 may send the alert signal to the data terminal communicatively coupled to the third electric field detector but not to the data terminal communicatively coupled to the alarming first electric field detector.

Figure 5D:
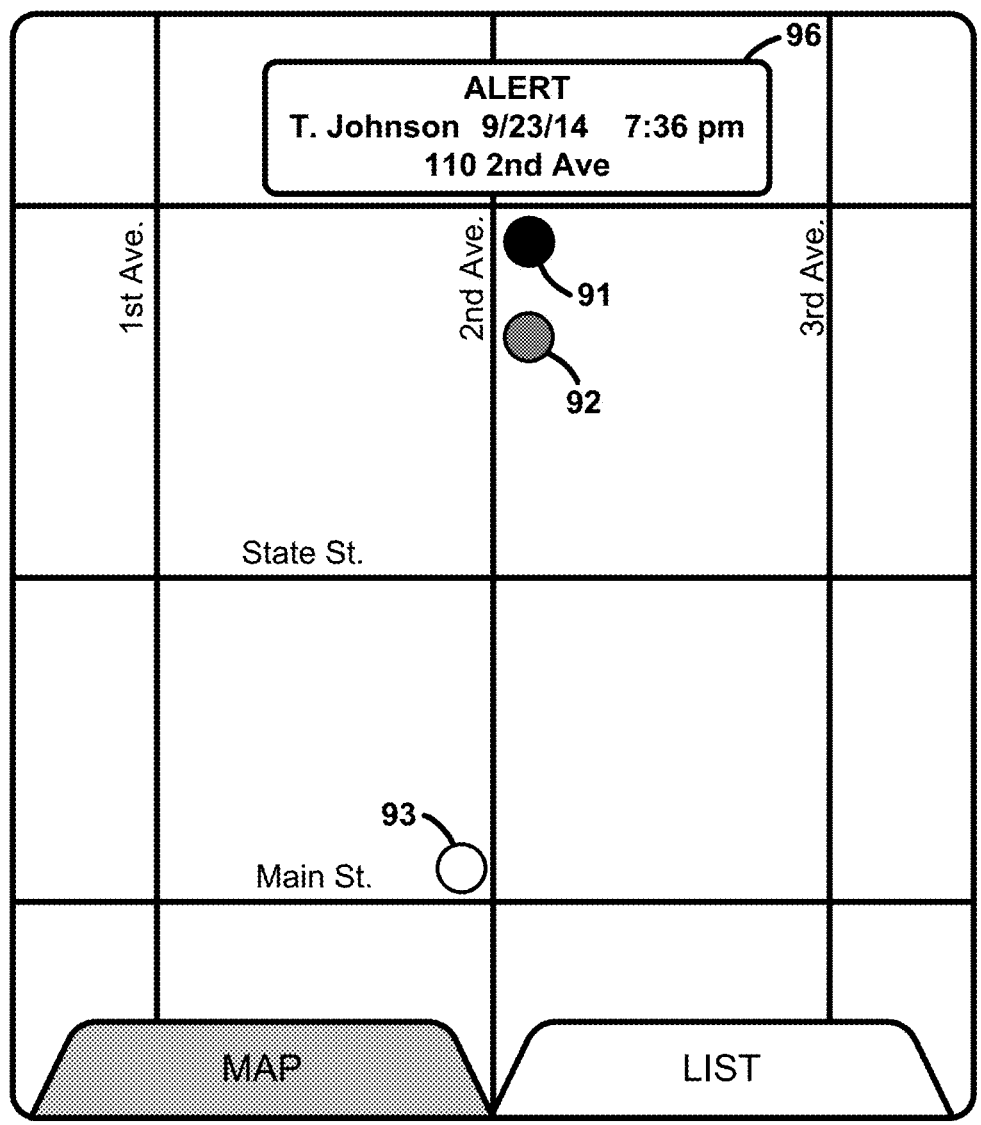

Server 20 may also send the alert signal to the data terminal of a supervisor, i.e., a remote data terminal. Thus, server 20 may cause the graphical user interface of the user's display terminal (as well as the third local data terminal) to responsive display alert message 96, as shown in FIG. 5D. In the illustrative example, alert message 96 includes text indicia of the current status of the second electric field detector. Further, the user may press the alert message to center the map on the alarming electric field detector.

At the bottom of the displays in FIGS. 5A-5D are "Map" and "List" buttons to allow the user to switch between the map component and the list component of the graphical user interface. Upon the user pressing the list button, the data terminal may transmit to server 20 data representative of a request to display the list component, and server 20 may responsively cause the graphical user interface to present a list display shown in FIG. 5E.

The list display may present the indicia of the status data of the monitored electric field detectors as blocks of text, with each block of text corresponding to one of the monitored electric field detectors. In FIG. 5E, the presented indicia of the status data 98A, 98B, 98C, 98D, and 98E are displayed as five blocks of status data.

The indicia of status data presented on the list display can be sorted according to in a number of ways. In one example, blocks of status data corresponding to alarming electric field detectors may be higher on the list than blocks corresponding to electric field detectors that are not alarming. Additionally or alternatively, the user may interact with the graphical user interface to filter from the list display the presented indicia of the status data corresponding to electric field detectors that are not alarming. In this manner, the user may be able to identify status data associated with alarming electric field detectors, which may assist the user in thereby in directing repair teams to certain areas and/or in identifying and securing electrical equipment supplying detected high-voltage power sources.

In the example illustrated in FIG. 5E, indicia of the status data 98D display is indicative of an associated electric field detector having a low battery. To provide such indicia, server 20 may have received status data for that electric field detector data indicative of a charge level of the electric field detector's and have determined that the charge level was less than or equal to a threshold charge level. Alternatively, the local data terminal communicatively coupled to the electric field detector could have made that determination, in which case the status signal may have included data indicative of the battery level being less than or equal to the threshold battery level.

Figure 6:
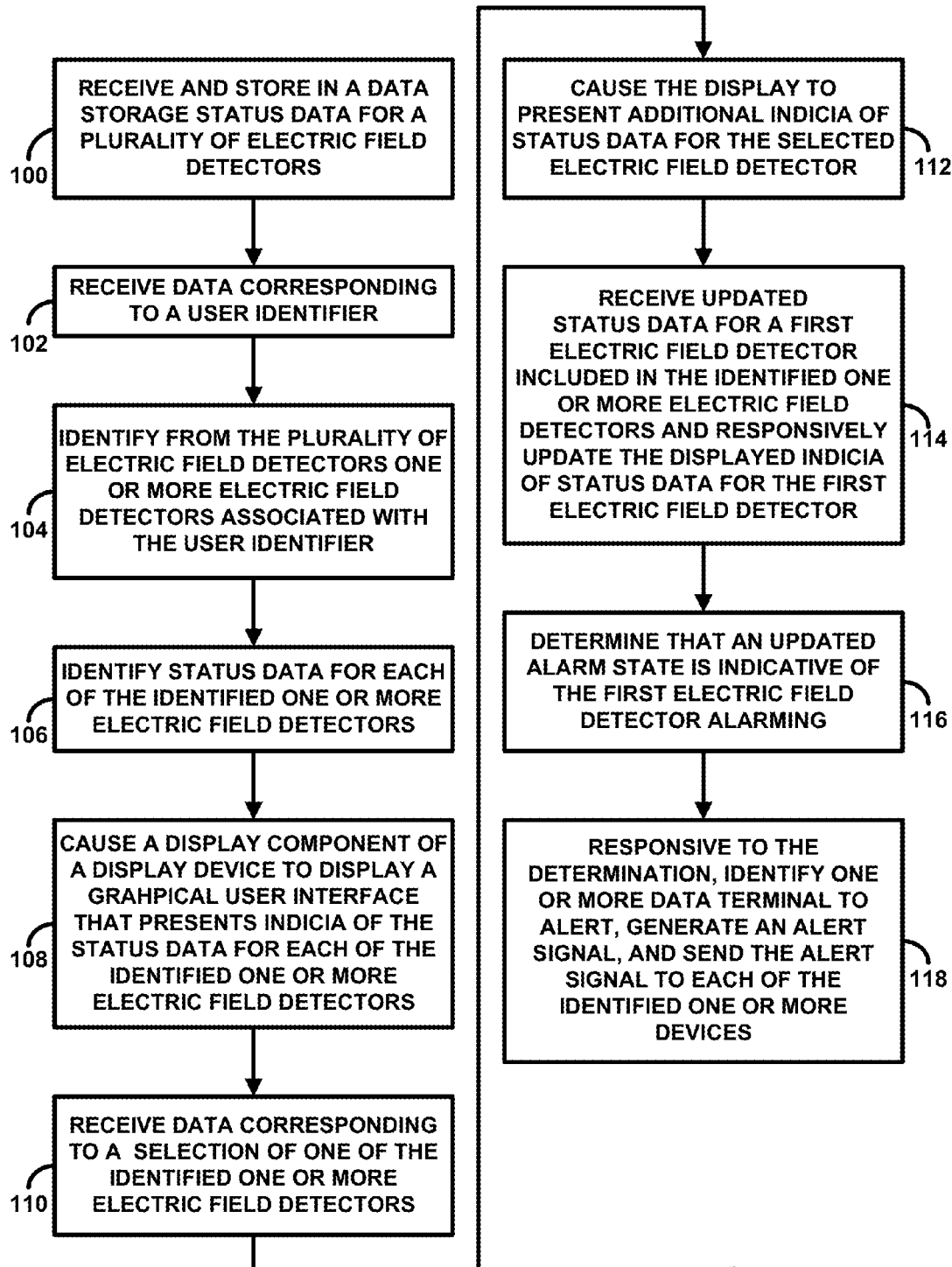
FIGS. 6 and 7 are flow diagrams depicting functions that can be carried out in accordance with the present disclosure.

FIG. 6 shows functions that can be carried out in accordance with a representative method. The functions shown can be carried out in the order shown or in another order. Additionally or alternatively, the functions shown may be combined or distributed in various ways. For illustrative purposes, the method of FIG. 6 is described with respect to a computing system, such as server 20.

Beginning at block 100, a computing system receives and stores in a data storage status data for a plurality of electric field detectors. Next, at block 102, the computing system receives data corresponding to a user identifier. At block 104, the computing system identifies from the plurality of electric field detectors one or more electric field detectors associated with the user identifier.

At block 106, the computing system identifies status data for each of the identified one or more electric field detectors. As previously described, the status data for each electric field detector includes data indicative of at least (i) a location of the electric field detector and (ii) an alarm state of the electric field detector. At block 108, the computing system causes a display component of a device to display a graphical user interface that presents indicia of the status data for each of the identified one or more electric field detectors.

Moving now to block 110, the computing system receives data corresponding to a selection of one of the identified one or more electric field detectors. At block 112, the computing system, responsive to receiving the selection, causes the display to present additional status data for the selected electric field detector.

Now at block 114, the computing receives and stores in the data storage updated status data for a first electric field detector, with the first electric field detector being one of the identified one or more electric field detectors. At block 116, the computing system determines that an updated alarm state of the first electric field detector is indicative of the electric field detector alarming. In this case, the updated status data includes data indicative of the updated alarm state. Responsive to making that determination, the computing system at block 118 identifies one or more data terminals to alert, generates an alert signal, and sends the alert signal to each of the identified one or more devices. The alert signal includes data indicative of the first electric field detector alarming, with such data including at least a portion of the status data for the first electric field detector. Further, sending the alert signal to the identified one or more devices to alert may cause each such device to provide at least one of a visual output, an audible output, or a tactile output.

It should be noted that components of the computing system performing identification functions described in the method above may do so in a number of ways. For example, a processor, such as processor 72 described with respect to FIG. 4, may perform identification functions by retrieving and/or accessing data stored in data storage, such as reference data 78 described with respect to FIG. 4. The processor may then process and/or aggregate the retrieved/accessed data, and the processor may then select from the processed/aggregated data a subset of data that is associated with a value for a particular field, such as data corresponding to a particular user profile or data corresponding to a particular electric field detector.

Figure 7:
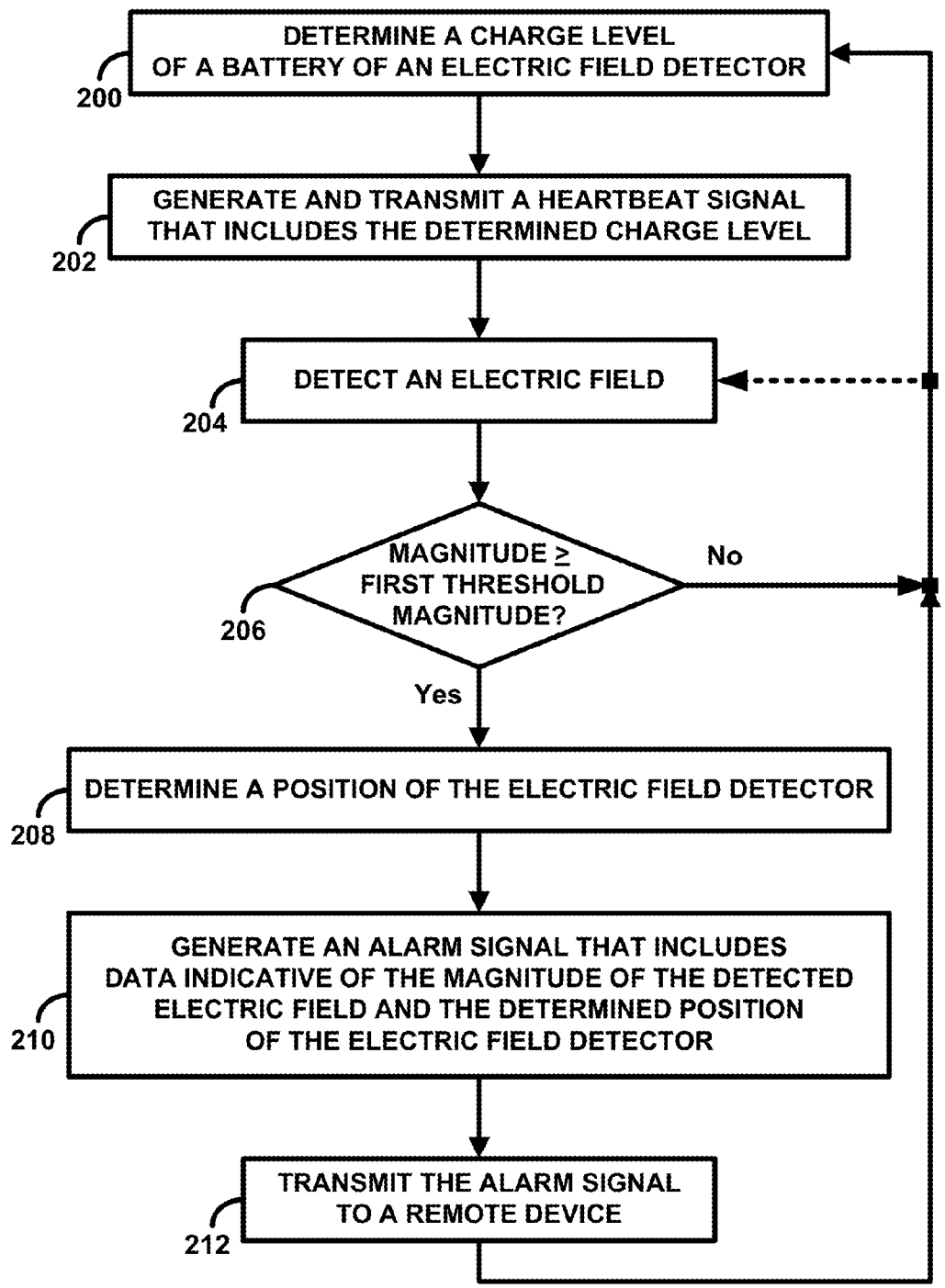

Finally, FIG. 7 shows functions that can be carried out in accordance with another representative method. The functions shown can be carried out in the order shown or in another order. Additionally or alternatively, the functions shown may be combined or distributed in various ways. For illustrative purposes, the method of FIG. 7 is described with respect to an electric field detector, such as electric field detector 14.

Beginning at block 200, the electric field detector determines a charge level of a battery of an electric field detector. At block 202, the electric field detector generates and transmits a heartbeat signal that includes the determined charge level. In some examples, the heartbeat signal may also include data indicative of whether the electric field detector is alarming (e.g., whether the electric field detector has detected an electric field having a magnitude that is greater than or equal to at least a first threshold).

At block 204, the electric field detector detects an electric field. The electric field then determines whether a magnitude of the detected electric field is greater than or equal to at least a first threshold magnitude, at block 206. If the magnitude of the detected is less than the first threshold magnitude, then the electric field detector may reperforms the steps of block 200 or block 204.

On the other hand, if the magnitude of the detected electric field is greater than or equal to at least the first threshold magnitude, the electric field detector proceeds to block 208 and determines a position of the electric field detector. Note that embodiments in which the electric field detector does not include a positioning component, such as locator component 42, the electric field detector may not perform the steps of block 208. Alternatively, the electric field detector may use an external positioning system to determine the position of the electric field detector.

Now at block 210, the electric field detector generates an alarm signal that includes data indicative of the magnitude of the detected electric field. In embodiments in which the electric field detector determined the position of the electric field at block 208, the alarm signal also includes the determined position. At block 212, the electric field detector transmits the alarm signal to a remote device, such as one of data terminals 14 described with respect to FIGS. 1 and 3.

Upon completing block 212, the electric field detector performs another iteration of the illustrated method by returning to block 200 or block 204. In this manner, the electric field detector may periodically determine the charge of the battery and send the heartbeat signal.

It should be understood that a computing device may have means for performing anyone of the method or functions described herein. For instance, a first example apparatus comprises means for detecting an electric field; determining that a magnitude of the detected electric field is greater than at least a first threshold magnitude; and responsive to determining that the magnitude of the detected electric field is greater than at least the first threshold magnitude, (i) generating by the electric field detector an alarm signal that includes data indicative of the magnitude of the detected electric field, and (ii) transmitting the alert signal from the electric field detector to a data terminal.

In one example, the first example apparatus further comprises means for determining a position of the electric field detector at a time at which the electric field detector detected the electric field, wherein the alarm signal includes data indicative of the determined position.

Additionally or alternatively, the first example apparatus further comprises means for (i) generating a heartbeat signal and (ii) transmitting to the remote device the heartbeat seat signal.

In another example, the first example apparatus further comprises means for determining a charge level of a battery of the electric field detector, wherein at least one the heartbeat signal or the alarm signal includes data indicative of the determined charge level.

In yet another example, the first example apparatus further comprises means for providing at least one of a visual output, an audible output, or a tactile output.

As another general example, a second example apparatus comprises means for receiving from a device data corresponding to a user identifier; means for identifying from a plurality of electric field detectors one or more electric field detectors associated with the user identifier; means for identifying status data for each of the identified one or more electric field detectors, wherein the status data for each electric field detector in the plurality of electric field detectors comprises data indicative of at least (i) a location of the electric field detector and (ii) an alarm state of the electric field detector; and means for causing a display component of the device to display a graphical user interface that presents indicia of the status data for each of the identified one or more electric field detectors.

In one example, the second example apparatus further comprises means for receiving data representative of a selection of one of the presented indicia; means for identifying, based on the selection, a selected electric field detector from the identified one or more electric field detectors; and means for presenting via the graphical user interface a message box that includes textual representations of the status data for the selected electric field detector.

In another example, the second example apparatus further comprises receiving data indicative of a request to filter the list such that the list is limited to presenting indicia of electric field detectors that are alarming; means for identifying, based on the alarm state for each of the identified one or more electric field detectors, a set of one of more electric field detectors that are not alarming; and means for removing from the graphical user interface the presented indicia corresponding to each electric field detector in the set of one or more electric field detectors.

In yet another example, the second example apparatus further comprises means for receiving updated status data for a first electric field detector, wherein the first electric field detector is one of the identified one or more electric field detectors, and wherein the updated status data comprises an update to at least one of (i) the location of the first electric field detector or (ii) the alarm state of the first electric field detector; and means for updating, responsive to receiving the updated status data, the indicia of the status data for the first electric field detector to reflect the updated status data.

In still another example, the second example apparatus further comprises means for receiving updated status data for a first electric field detector, wherein the first electric field detector is one of the identified one or more electric field detectors, and wherein the updated status data comprises an updated alarm state of the first electric field detector; means for determining that the alarm state includes data indicative of the first electric field detector alarming; and, responsive to the determining, (i) means for identifying one or more devices to alert; (ii) means for generating an alert signal, wherein the alert signal includes data indicative of the first electric field alarming; and (iii) means for send the alert signal to each of the one or more devices to alert, thereby causing each of the identified one or more devices to provide at least one of a visual output, an audible output, or a tactile output.

Additionally or alternatively, the second example apparatus further comprises means for determining that the device is operating in a monitoring mode, wherein the device operates in the monitoring mode when it is not communicatively coupled to one of the electric field detectors included in the plurality of electric field detectors; and means for identifying, responsive to determining that the device is operating in the monitoring mode, the device as one of the one or more devices to alert.

It should be understood that for situations in which the embodiments discussed herein collect and/or use any personal information about users or information that might relate to personal information of users, the users may be provided with an opportunity to opt in/out of programs or features that involve such personal information (e.g., information about a user's preferences or a user's contributions to social content providers). In addition, certain data may be anonymized in one or more ways before it is stored or used, so that personally identifiable information is removed. For example, a user's identity may be anonymized so that no personally identifiable information can be determined for the user and so that any identified user preferences or user interactions are generalized (for example, generalized based on user demographics) rather than associated with a particular user With respect to any or all of the block diagrams, examples, and flow diagrams in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. A wearable electric field detector comprising:
an electric field detection component configured (i) to detect an electric field having a magnitude that is greater than or equal to at least a first threshold magnitude and (ii) to provide at least one output indicative of a magnitude of a detected electric field when the magnitude of the detected electric field is greater than or equal to the first threshold magnitude;
a communication interface configured to communicate with a remote device; and
a controller configured to transmit via the communication interface an alarm signal in response to the electric field detection component providing the at least one output, wherein the alarm signal includes data indicative of the magnitude of the detected electrical field.

2. The wearable electric field detector of claim 1, wherein the communication interface comprises a transmitter component configured to wirelessly transmit the alarm signal.

3. The wearable electric field detector of claim 2, wherein a transmission range of the transmitter is about one meter.

4. The wearable electric field detector of claim 2, wherein a transmission range of the transmitter is between about one meter and about one hundred meters.

5. The wearable electric field detector of claim 1, wherein the communication interface comprises a transmitter component configured to wirelessly transmit the alarm signal.

6. The wearable electric field detector of claim 1, further comprising at least one of a visual output component, an audible output component, or a tactile output component, and wherein the at least one output comprises at least one of a visual output, an audible output, or a tactile output.

7. The wearable electric field detector of claim 1, further comprising a battery, wherein the controller is further configured to cause the communication interface to periodically transmit a heartbeat signal that includes information indicative of a charge level of the battery.

8. The wearable electric field detector of claim 1, further comprising a global position system (GPS) receiver configured to determine a location of the wearable electric field detector, wherein the alarm signal further comprises a position of the wearable electric field detector at a time at which the electric field detection circuitry detected the detected electric field.

9. The wearable electric field detector of claim 8, wherein the controller is further configured to cause the communication interface to periodically transmit a heartbeat signal, wherein the heartbeat signal includes data indicative of a position of the wearable electric field detector at a time prior to transmission of the heartbeat signal.

10. The wearable electric field detector of claim 1, wherein the wearable electric field detector is configured to be worn on a body of a user.

11. A method comprising:
   detecting, by a wearable electric field detector, an electric field;
   determining that a magnitude of the detected electric field is greater than at least a first threshold magnitude; and
   responsive to the determining, (i) generating by the wearable electric field detector an alarm signal that includes data indicative of is selected from a plurality of alarm signals based on the magnitude of the detected electric field, and (ii) transmitting the alarm signal from the wearable electric field detector to a data terminal.

12. The method of claim 11, further comprising determining a position of the wearable electric field detector at a time at which the wearable electric field detector detected the electric field, wherein the alarm signal includes data indicative of the determined position.

13. The method of claim 11, wherein the alarm signal comprises one of: a first alarm signal when the magnitude of the electric field is greater than or equal to the first threshold magnitude and less than a second threshold magnitude, a second alarm signal when the magnitude of the electric field is greater than or equal to the second threshold magnitude and less than a third threshold magnitude, or a third alarm signal when the electric field being greater than or equal to the third threshold magnitude.

14. The method of claim 11, wherein the data terminal is one of a mobile phone, a smartphone, or a tablet computer.

15. The method of claim 11, further comprising the wearable electric field detector (i) generating a heartbeat signal and (ii) transmitting to the remote device the heartbeat seat signal.

16. The method of claim 15, determining a position of the wearable electric field detector, wherein the heartbeat signal includes data indicative of the determined position.

17. The method of claim 15, determining a charge level of a battery of the wearable electric field detector, wherein at least one the heartbeat signal or the alarm signal includes data indicative of the determined charge level.

18. The method of claim 11, further comprising, in response to determining that the magnitude of the detected electric field is greater than or equal to at least a first threshold magnitude, the wearable electric field detector providing at least one of a visual output, an audible output, or a tactile output.

19. A non-transitory computer readable medium having stored thereon instructions executable by a computing system to carry out functions comprising:
   receiving, by a wearable electric field detector, an indication of a magnitude of a detected electric field;
   determining that the magnitude of the detected electric field is greater than or equal to at least a threshold magnitude; and
   responsive to determining that the magnitude of the detected electric field is greater than or equal to at least the threshold magnitude, (i) generating, at the wearable electric field detector, an alarm signal that includes data indicative of the magnitude of the detected electric field, and (ii) transmitting, from the wearable electric field detector, the alarm signal to a data terminal.

20. The non-transitory computer readable medium of claim 19, wherein, responsive to the receiving the indication, the functions further comprise determining a position of the wearable electric field detector, wherein the alarm signal further includes data indicative of the determined position.

* * * * *